(12) United States Patent
Lee et al.

(10) Patent No.: US 10,792,518 B2
(45) Date of Patent: Oct. 6, 2020

(54) SYSTEM AND DEVICE FOR IMPROVED ULTRASOUND CAVITATION MAPPING

(71) Applicant: The Board of Trustees of the Leland Stanford Junior University, Palo Alto, CA (US)

(72) Inventors: Taehwa Lee, Palo Alto, CA (US); Juergen K. Willmann, Stanford, CA (US); Jeremy Joseph Dahl, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 280 days.

(21) Appl. No.: 16/027,696

(22) Filed: Jul. 5, 2018

(65) Prior Publication Data

US 2019/0009108 A1  Jan. 10, 2019

Related U.S. Application Data

(60) Provisional application No. 62/529,414, filed on Jul. 6, 2017.

(51) Int. Cl.
*A61B 5/00* (2006.01)
*A61N 7/00* (2006.01)
(Continued)

(52) U.S. Cl.
CPC ............ *A61N 7/00* (2013.01); *A61B 8/085* (2013.01); *A61B 8/481* (2013.01); *A61B 8/5207* (2013.01);
(Continued)

(58) Field of Classification Search
None
See application file for complete search history.

(56) References Cited

U.S. PATENT DOCUMENTS

2015/0005756 A1* 1/2015 Tillander ................. A61N 7/02
606/27

OTHER PUBLICATIONS

The direct estimation of sound speed using pulse-echo ultrasound, Martin E. Anderson and Gregg E. Trahey, 3099 J. Acoust. Soc. Am. 104 (5).

(Continued)

*Primary Examiner* — Joel F Brutus
(74) *Attorney, Agent, or Firm* — Lumen Patent Firm

(57) ABSTRACT

A passive cavitation mapping method is provided that includes capturing a channel signal from at least one ultrasound transducer in an array of ultrasound transducers, isolating a cavitation signal in the channel signal, time-gating the channel signal about the cavitation signal, computing a time-delay between neighboring the cavitation signals in adjacent the channel signals, computing a modified parabolic fit to the square of the arrival times, where the modified parabolic fit includes a coordinate transformation using an x location of a leading edge of wavefronts of the cavitation signal and a maximum arrival time of the cavitation signal, extracting a location of a cavitation signal source at point (x, z) in the coordinate transformation, computing a cavitation magnitude for each non-eliminated cavitation signal, creating a passive cavitation map by convolving the cavitation magnitude and the source location with an uncertainty function, and using the cavitation map for therapeutic ultrasound applications.

4 Claims, 12 Drawing Sheets

(51) Int. Cl.
*A61B 8/08* (2006.01)
*A61B 17/00* (2006.01)
(52) U.S. Cl.
CPC .. *A61B 8/5269* (2013.01); *A61B 2017/00106* (2013.01); *A61N 2007/0039* (2013.01); *A61N 2007/0065* (2013.01); *A61N 2007/0095* (2013.01)

(56) References Cited

OTHER PUBLICATIONS

A Novel Method for Angle Independent Ultrasonic Imaging of Blood Flow and Tissue Motion, Laurence N. Bohs, Gregg E. Trahey, IEEF Transactions on Biomedical Enginfering. C'OL 18. No. 3.
A Class of Algorithms for Fast Digital Image Registration Daniel I. Barnea,, Harvey F. Silverman, Transactions on Computers, vol. c-21, No. 2.
Real-Time Two-Dimensional Blood Flow Imaging Using an Autocorrelation Technique, Chihiro Kasai, Koroku Namekawa, Akira Koyano, and Ryozo Omoto, IEEE Transactions on Sonics and Uiltrasonics, vol. SU-32, No. 3.
An Axial Velocity Estimator for Ultrasound Blood Flow Imaging, Based on a Full Evaluation of the Doppler Equation by Means of a Two-Dimensional Autocorrelation Approach, Thanasis Loupas, J. T. Powers, and Robert W. Gill, IEEE Transactions on Ultrasonics, Ferroelectrics, and Frequency Control.

* cited by examiner

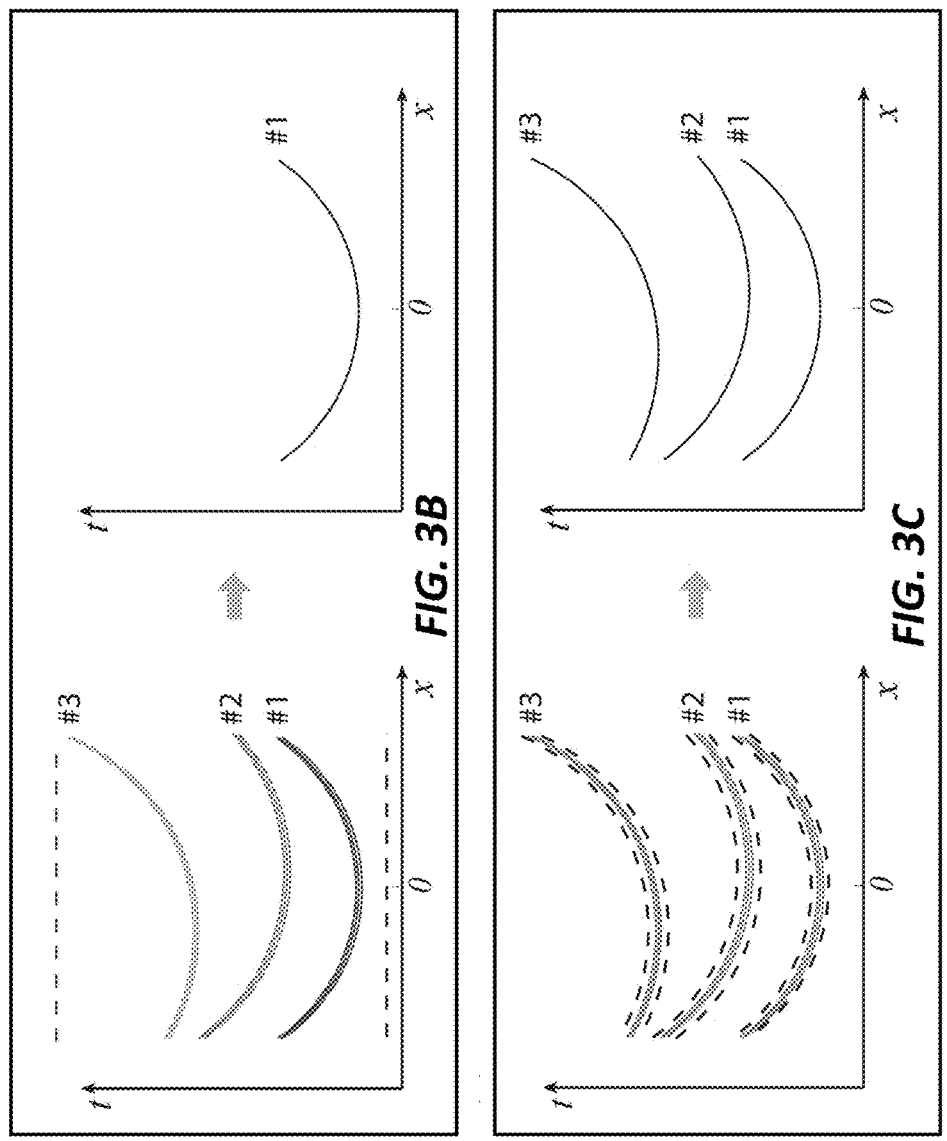
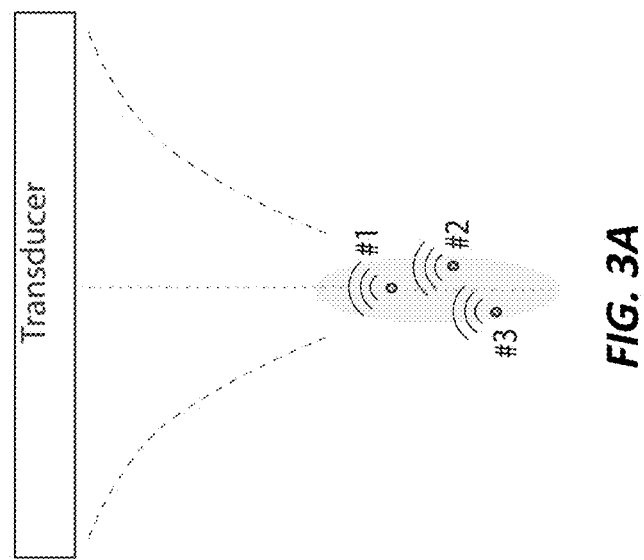
FIG. 3A
FIG. 3B
FIG. 3C

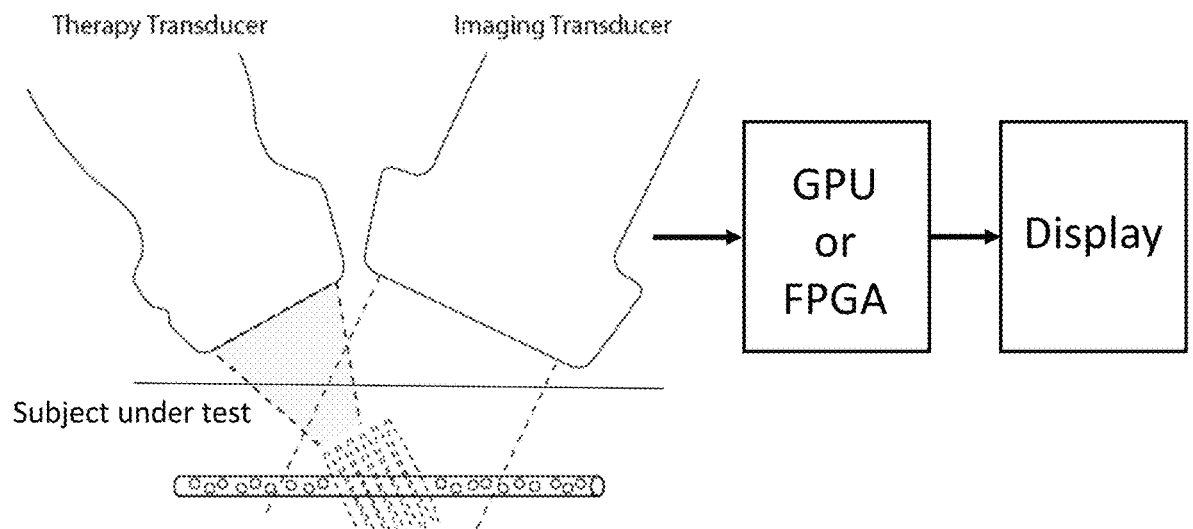
FIG. 4A
FIG. 4B
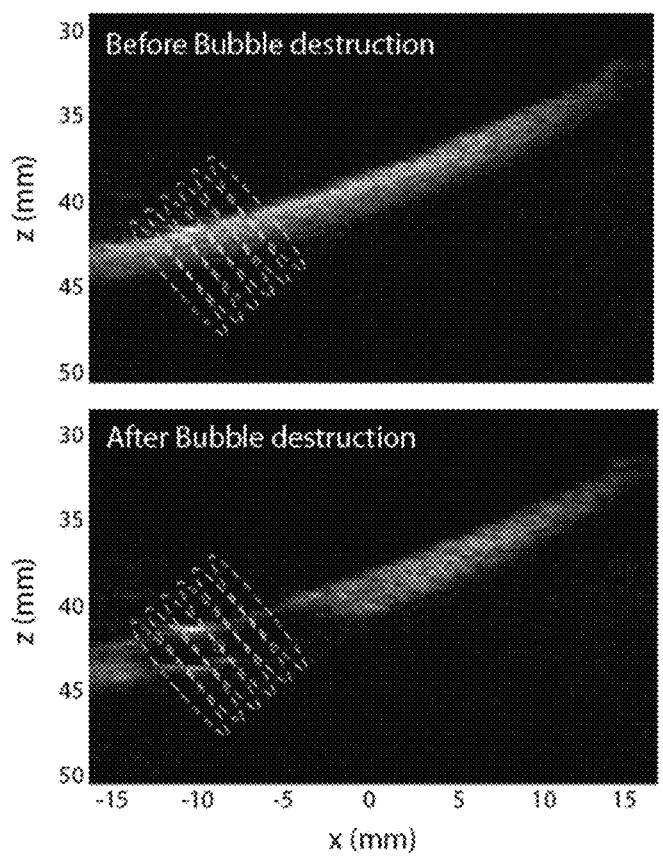

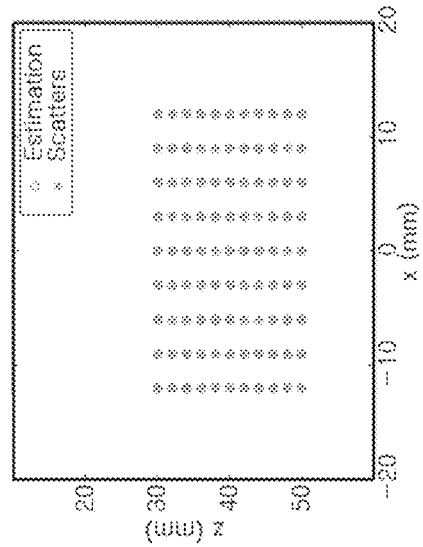
FIG. 6A Anderson-Trahey method
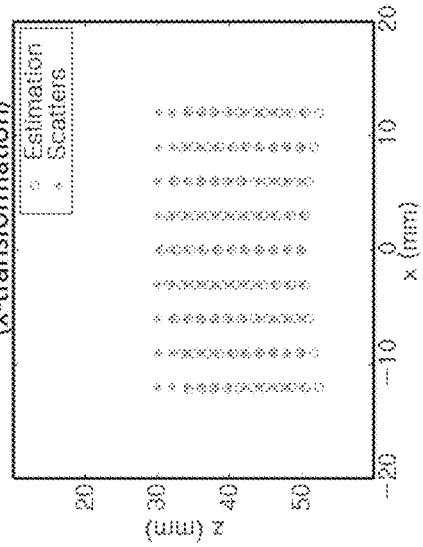
FIG. 6B Anderson-Trahey method (x-transformation)
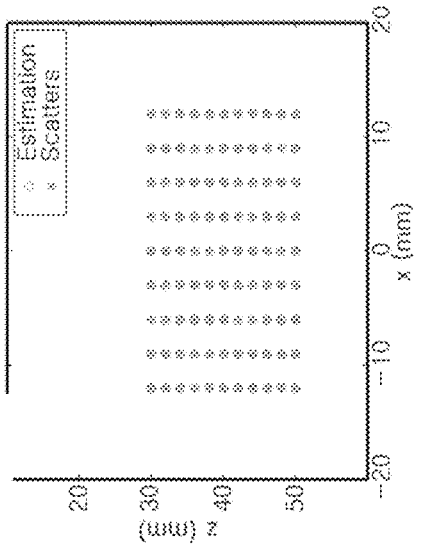
FIG. 6C Modified parabola fit
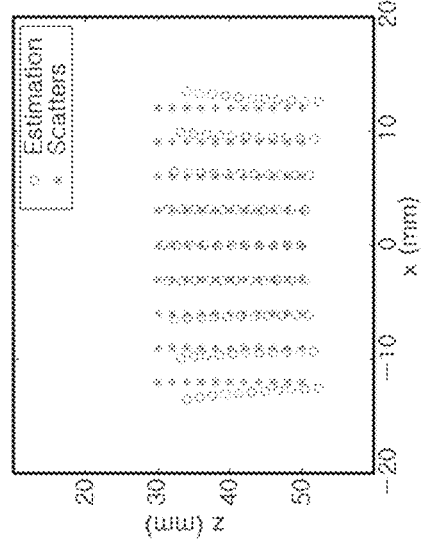
FIG. 6D Anderson-Trahey method
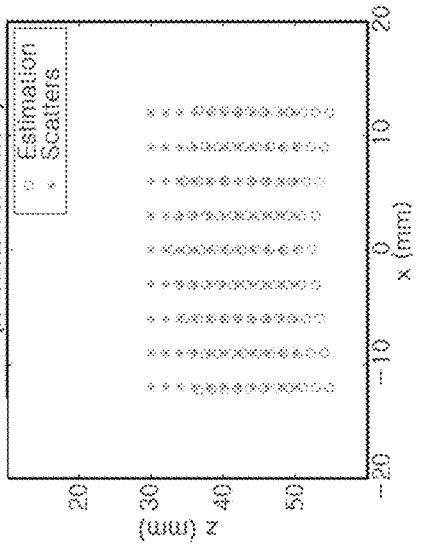
FIG. 6E Anderson-Trahey method (x-transformation)
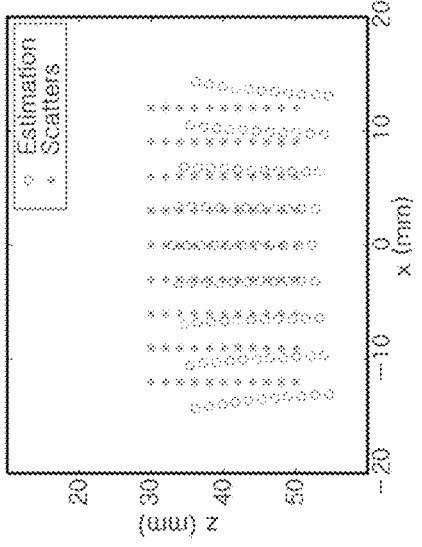
FIG. 6F Modified parabola fit

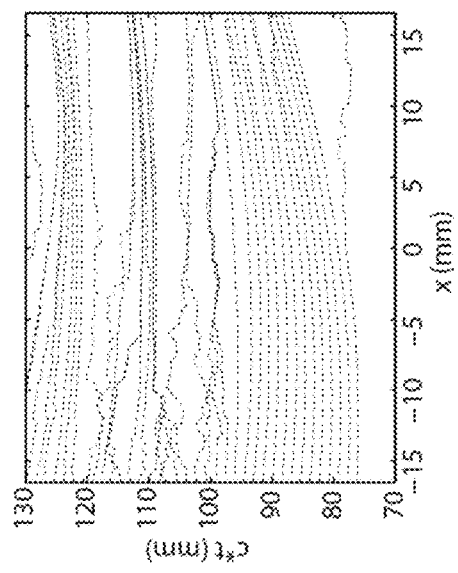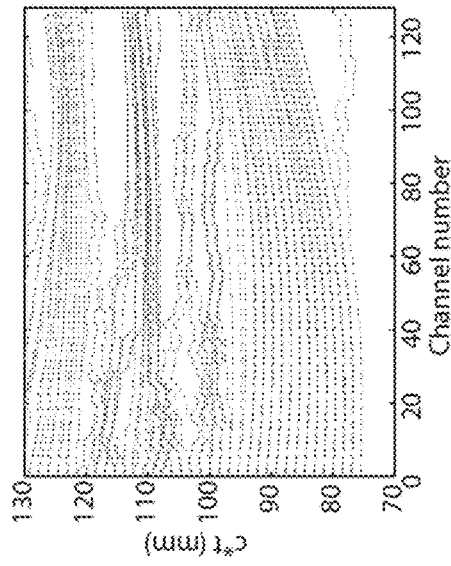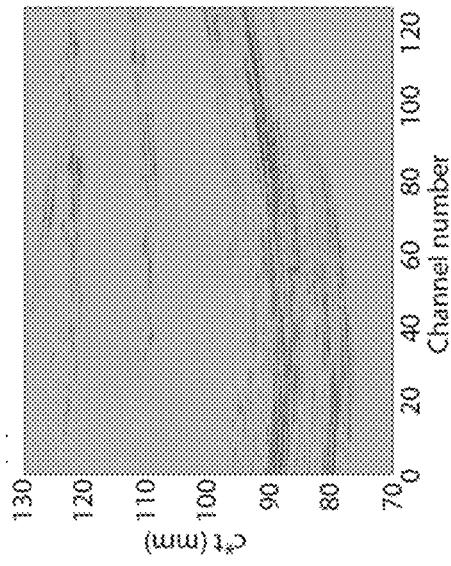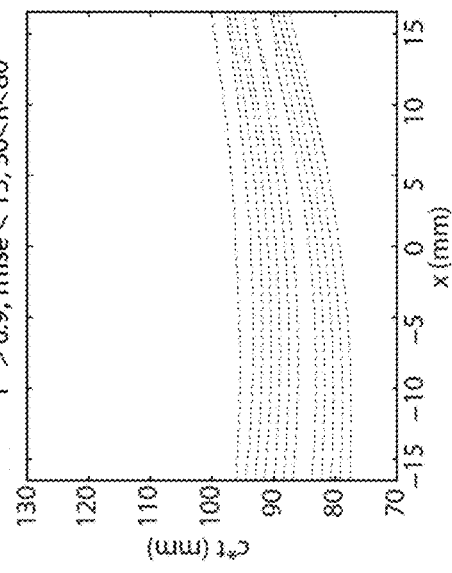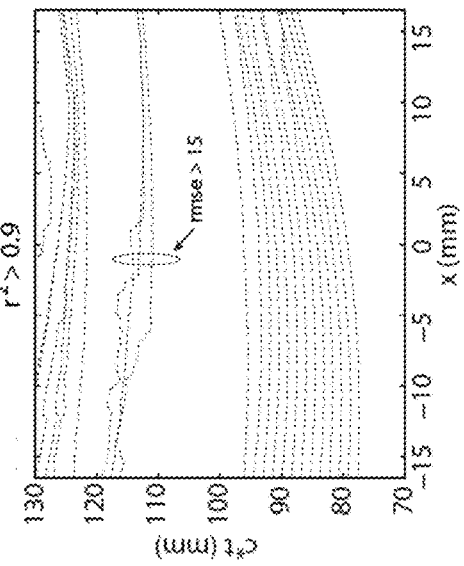
FIG. 8A
FIG. 8B
FIG. 8C
FIG. 8D
FIG. 8E
FIG. 8F

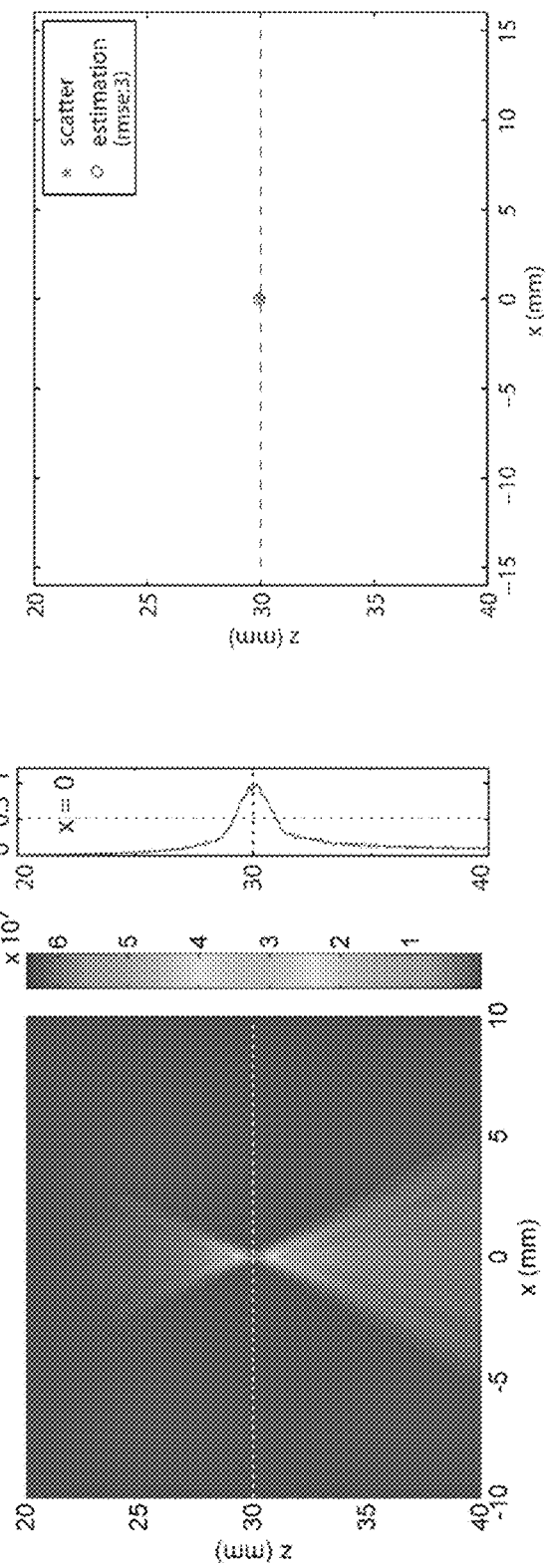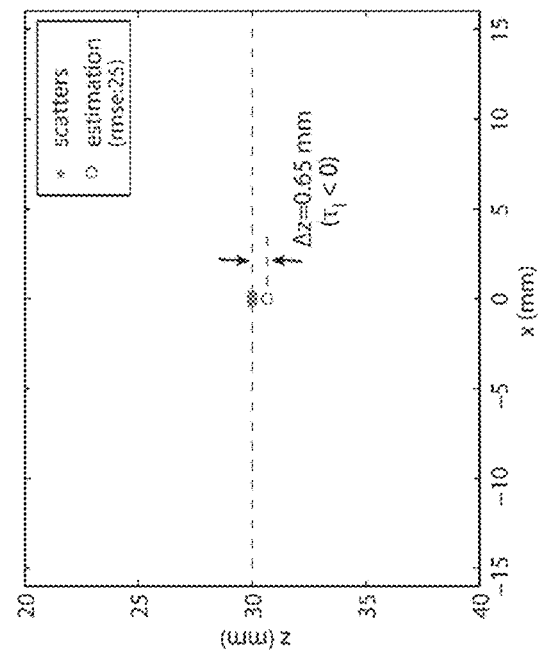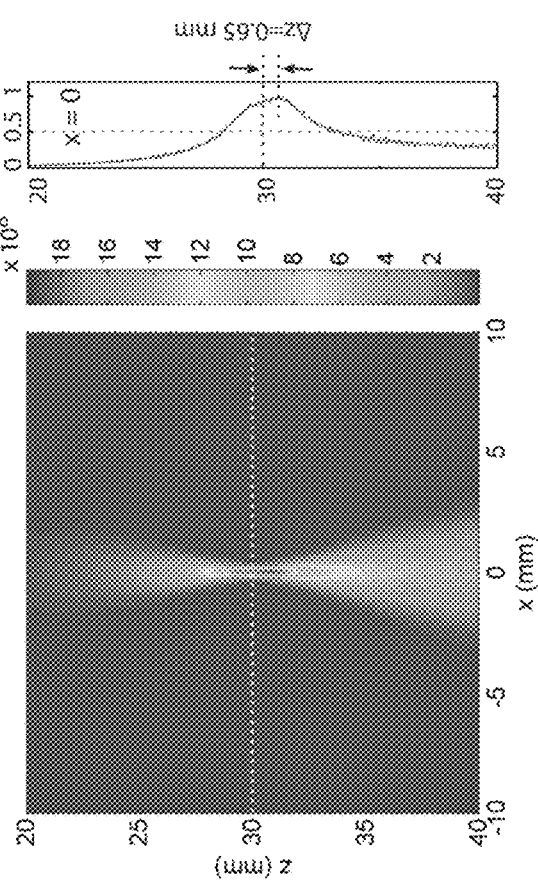
FIG. 10A
FIG. 10B
FIG. 10C
FIG. 10D

SYSTEM AND DEVICE FOR IMPROVED ULTRASOUND CAVITATION MAPPING

CROSS-REFERENCE TO RELATED APPLICATIONS

This application claims priority from U.S. Provisional Patent Application 62/529,414 filed Jul. 6, 2017, which is incorporated herein by reference.

STATEMENT OF GOVERNMENT SPONSORED SUPPORT

This invention was made with Government support under contract EB022298 awarded by the National Institutes of Health. The Government has certain rights in the invention.

FIELD OF THE INVENTION

The present invention relates generally to ultrasound cavitation mapping. More particularly, the invention relates to a method of passively listening to a cavitation event, where there is no timing associated with the event, where the received signal is processed using a modified parabolic fit algorithm to determine the location of the event.

BACKGROUND OF THE INVENTION

Cavitating bubbles can produce localized mechanical effects, making them useful for various ultrasound-based applications ranging from sonoporation-induced drug delivery and blood-brain barrier opening to surface cleaning. Outcomes produced by these applications are determined by the cavitation activities associated with stable oscillations or inertial growth/collapse of bubbles, often referred to as stable and inertial cavitation, respectively. For therapeutic ultrasound applications, monitoring cavitation is critical for evaluation of therapeutic outcomes, allowing users to reach a particular threshold of therapy for effective treatment or to avoid overtreatment. Conventional monitoring methods such as B-mode and contrast-enhanced ultrasound imaging can localize bubbles under stable oscillation. These imaging methods are known as active cavitation imaging methods, where the pulses are designed to have a low mechanical index in order to avoid destruction of the bubbles and allowing echoes from the bubbles to be detected. However, these active imaging methods are incapable of monitoring short-lived transient bubbles that undergo inertial cavitation. Although ultrafast B-mode imaging has been shown to overcome this challenge by using frame rates higher than typical B-mode imaging, these methods, while providing information about the existence and location of bubbles, are unable to provide information that is useful for classifying stable/inertial cavitation. Moreover, such active cavitation imaging methods typically record echo signals when the therapeutic transducer is not transmitting, because the imaging pulses interfere with the acoustic emissions from the bubbles.

Unlike active cavitation imaging methods, passive cavitation imaging methods detect acoustic emissions from bubbles without using transmission pulses. Several studies have shown a significant correlation between cavitation signal levels and therapeutic outcomes. For example, increased broadband emissions correspond to increased ultrasound ablation volume. A study on ultrasound/microbubble-mediated drug delivery suggested that drug delivery outcomes were strongly correlated to inertial cavitation dose. They found that increasing ultrasound pressure leads to enhanced drug delivery in mice. However, these passive cavitation detection methods typically use a single element transducer that does not provide localized spatial information of cavitation, but rather cavitation signals spatially averaged within the focal volume. Recently, passive cavitation mapping (PCM) using an array of transducers has been introduced, allowing for both real-time mapping and quantification of cavitation sources producing nonlinear acoustic emissions. PCM has shown promise in therapy monitoring, which has been successfully implemented for monitoring of lesion formation by high intensity focused ultrasound (HIFU), drug delivery to tumors, and therapies in brain.

PCM algorithms are primarily based on time exposure acoustics (TEA), which utilizes fixed-focus delay-and-sum beamforming over a grid of points, followed by the time-averaging of the squared beamformed data. Here, the time average is capable of capturing cavitation signals composed of narrowband signals due to stable oscillation or broadband signals due to inertial cavitation that are emitted long after insonation pulses impact the bubbles. However, these TEA algorithms suffer from poor axial resolution due to a combination of the limited point spread function of the array transducer and bubble-bubble interactions. Notably, PCM-TEA exhibits a tail artifact, the appearance of an elongated region of cavitation energy beyond the focal region of the applied acoustic pulse, even though cavitation only occurs within the focal region. More recently, it was found that this is mainly an artifact of bubble interference rather than bubbles that are present behind the focal region. Inspired by recent advances in adaptive beamforming using constraints, researchers modified a robust Capon beamformer, also called the minimum variance distortionless response beamformer, for PCM to significantly reduce interference artifacts. The Capon beamformer, despite its promise for PCM, has several limitations. First, this beamformer requires high signal-to-noise ratio (SNR) to achieve the desired resolution, and reverts back to the delay-and-sum beamformer when the SNR is low. While promising results have been shown in phantoms and small animals, translation to human imaging with this technique will be difficult due to the presence of inhomogeneous tissue that decrease SNR from reverberation clutter and phase aberration. In addition, the technique minimizes the output power of the array for non-ideal signals rather than improving localization of the cavitation signals, thereby eliminating potential cavitation signals not occurring on the beamforming axis, such as cavitation signals due to sidelobes.

What is needed is a passive cavitation mapping method that is based on sound localization of multiple scatters of cavitation.

SUMMARY OF THE INVENTION

To address the needs in the art, a passive cavitation mapping method is provided that includes capturing, using an ultrasound scanning device, a channel signal from at least one ultrasound transducer in an array of ultrasound transducers, isolating, using the ultrasound scanning device, a cavitation signal in the channel signal, where the isolating comprises using a filtering method, time-gating the channel signal about the cavitation signal, computing a time-delay between neighboring the cavitation signals in adjacent the channel signals, where time-delays of the cavitation signals are accumulated to obtain arrival times of the cavitation signals, computing a modified parabolic fit to the square of the arrival times, where the modified parabolic fit comprises a coordinate transformation using an x location of a leading edge of wavefronts of the cavitation signal and a maximum arrival time of the cavitation signal, extracting a location of a cavitation signal source at a point (x, z) in the coordinate transformation, computing a cavitation magnitude for each the non-eliminated cavitation signal, creating a passive cavitation map by convolving the cavitation magnitude and the source location with an uncertainty function, and using the cavitation map for therapeutic ultrasound applications.

According to one aspect of the invention, the uncertainty function comprises a circularly Gaussian function.

In another aspect, the invention further includes eliminating spurious cavitation signals, using the computer, based on poor fit of the modified parabola.

According to one aspect, the invention further includes calculate a bubble lifetime of each the non-eliminated cavitation signal, using the computer, and eliminating cavitation signals that negative lifetimes limits.

BRIEF DESCRIPTION OF THE DRAWINGS

FIGS. 3A-3C show (3A) cavitation emission from the three representative point scatters within the focus, labelled as #1, 2, and 3. (3B) RF channel data showing the corresponding coherent spherical wave patterns. The scattering intensity detected is assumed to be the strongest from the scatter #1. The dashed lines indicate the time domain used in cross correlation for arrival-time profile extraction. The extracted arrival-time profile through cross correlation over the entire time domain, corresponding to the dominant scatter. (3C) The same RF channel data, but with each wave pattern surrounded by a time-gated window for cross correlation (dashed lines). The extracted arrival-time profiles through the time gating approach, according to the current invention.

FIGS. 4A-4B show (4A) Schematics of a composite device consisting of a low-frequency therapy transducer and a high-frequency imaging transducer. The therapy transducer electronically steers its focus for destruction of bubbles in a vessel phantom, while the imaging transducer is used for B-mode imaging and passive cavitation imaging. (4B) B-mode images before bubble destruction (top) and after bubble destruction (bottom). The dashed ellipse indicates the focal spots of the therapy transducer, with the six focal spots each spaced with 1.2 mm, according to the current invention.

FIGS. 6A-6F show source localization using the modified parabola fit, compared to the Anderson-Trahey method with and without x-coordinate transformation. Two types of scatters are used: typical pulse-echo scatters (6A), (6B) and (6C), and cavitation-mimicking scatters with a constant time delay corresponding to assumed bubble lifetime (3 μs) (6D), (6E), and (6F). Regardless of the types and location, the modified parabola fit shows excellent localization, while estimation by the original Anderson-Trahey method produces significant errors for off-axis scatters closer to the transducer. The errors are worse for the cavitation mimicking scatters due to the delay associated with bubble lifetime.

FIGS. 8A-8F show extraction of multiple arrival-time profiles. (8A) Raw RF channel data used for the extraction. (8B) Time-gated windows (1 μs) encompassing signals corresponding to each arrival-time profile. (8C) Extracted arrival-time profiles. (8D) Arrival-time profiles with $r^2>0.9$. (8E) Arrival-time profiles with $r^2>0.9$ and root-mean-square error (rmse) <15 mm$^2$. (8F) Arrival-time profiles with $r^2>0.9$ and rmse of <15 mm$^2$, and 30<R<80 mm, where R is the radius of curvature, according to the current invention.

FIGS. 10A-10D show the effect of bubble-bubble interactions on source localization. Passive cavitation mapping based on time exposure acoustics (PCM-TEA) for a single scatter (10A) and interacting multiple scatters, 11 scatters laterally spaced with 0.05 mm (10C). The channel data used is simulated by using a 7.8 MHz transducer in a pulse-echo mode. The axial resolution for the single scatter is 1.8 mm of FWHM (~9λ), while the axial width for the multiple scatters is 4.84 mm of FWHM (~24.5λ) with its peak shift of Δz=0.65 mm. Corresponding source localization for the single scatter (10B) and multiple scatters (10D). Source location of the single scatter is accurately estimated with a high fit quality of rmse <5, whereas the closely-packed multiple scatters are identified as a single source, whose axial location is overestimated by the peak shift identified in PCM-TEA. The interacting multiple scatters exhibit a low fit quality of rmse >25, and the estimated source location leads to overestimation of receive time and thereby a negative bubble lifetime $\tau_l<0$), according to the current invention.

DETAILED DESCRIPTION

Disclosed herein is a method to adapt a speed of sound estimation technique to perform passive cavitation mapping based on cavitation source localization. The axial resolution of passive cavitation imaging by source localization is significantly improved by eliminating factors contributing to the tail artifact. According to the invention, cavitation sources are localized by applying a polynomial fit to arrival-time profiles of the cavitation signals, which is not limited by the axially-elongated point spread function of the passive imaging transducer. Furthermore, the tail artifact arising from bubble-bubble interactions can be effectively suppressed based on analysis on fitting quality and bubble lifetime, thus further improving the imaging quality.

Upon insonification with an imaging pulse, an ideal stationary point target reflects a spherical wave. The arrival times of the backscattered echoes as they return to a linear array of transducer elements are based on the path length differences between the reflection point and the transducer elements:

$$t(x_i) = \frac{\sqrt{(x_i - x_t)^2 + y_t^2 + z_t^2}}{c}, \tag{1}$$

where $(x_t, y_t, z_t)$ is the target location, c is the sound speed, and $x_i$ is the location of transducer element, i. M. E. Anderson and G. E. Trahey, "The direct estimation of sound speed using pulse-echo ultrasound," Journal of the Acoustical Society of America, vol. 104, no. 5, pp. 3099-3106, November 1998 is incorporated by reference in its entirety herein, and is referred to as "previous researchers" and "previous methods" throughout this disclosure, where previous researchers showed that the square of the arrival times is represented by a parabola, $$t^2(x_i) = p_1 x_i^2 + p_2 x_i + p_3, \tag{2}$$

where the coefficients of the parabola depend on the location of the target and the speed of sound of the propagation medium as follows:

$$p_1 = \frac{1}{c^2}, \tag{3}$$

$$p_2 = -\frac{2x_t}{c^2}, \text{ and}$$

$$p_3 = \frac{x_t^2 + y_t^2 + z_t^2}{c^2}.$$

In pulse-echo ultrasound, a parabolic fit to the square of the arrival-time profile of the reflected waves was used to estimate the speed of sound of a medium as well as infer the position of the insonified target (this method, however, was primarily utilized for sound speed estimation).

Previous researchers further showed that the estimation of speed of sound and position were not limited to point targets, but could also be estimated from the reflections from diffuse scatterers, such as those that give rise to speckle in B-mode ultrasound. Accurate usage of this approach requires that the transit time of the echo from the target to the transducer be well-characterized.

Figure 1A:
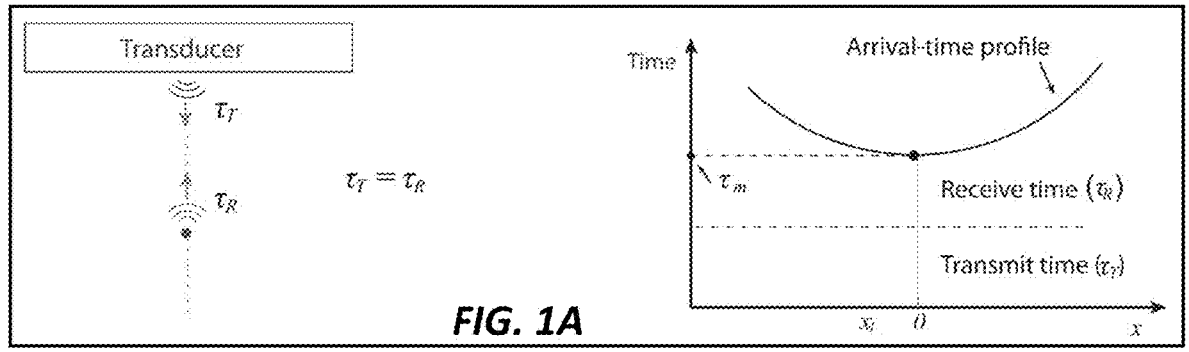
FIGS. 1A-1C show (1A) pulse and echo for a scatter on the beam axis, where the receive time is equal to the transmit time, i.e., $\tau_{RX}=\tau_{TX}$. (1B) Pulse and echo for a scatter off the beam axis, where the receive time cannot be easily determined because it is not equal to the transmit time, i.e., $\tau_{RX}\neq\tau_{TX}$. (1C) Acoustic emission from cavitation, where there exists a time-delay between the transmit event and the receive event, corresponding to the bubble lifetime. The minimum transit time of the acoustic emission at the transducer surface includes the bubble lifetime ($\tau_l$), i.e., $\tau_m=\tau_{RX}+\tau_{TX}+\tau_l$, according to the current invention.
Figure 1B:
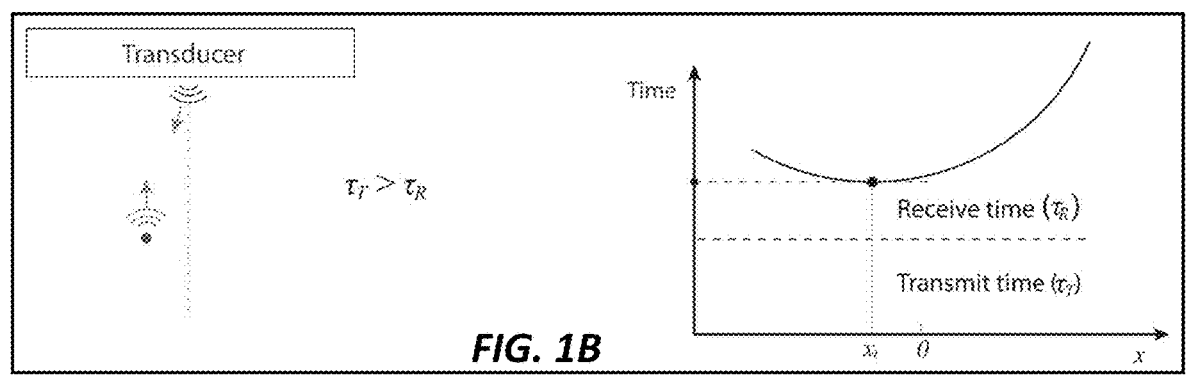

For pulse-echo scatterers, the arrival times measured using a synchronous system are composed of a transmit time (from transducer array to a scatter) and a receive time (from a scatter to transducer array). In this method, the arrival-times are computed with respect to the receive times. To compute accurate arrival times, the method is limited to scattering events on the axis of the ultrasound beam so that both the transmit ($\tau_{TX}$) and receive ($\tau_{RX}$) times are equal to half the minimum roundtrip, or transit, time ($\tau_m$) of the pulse, i.e., $\tau_{TX}=\tau_m/2$ and $\tau_{RX}=\tau_{TX}$, as illustrated in FIG. 1A. This method is unsuitable to scatterers off the axis of an ultrasound beam because the transmit time is not equal to the receive time, i.e., $\tau_{RX}\neq\tau_{TX}$, as shown in FIG. 1B.

Figure 1C:
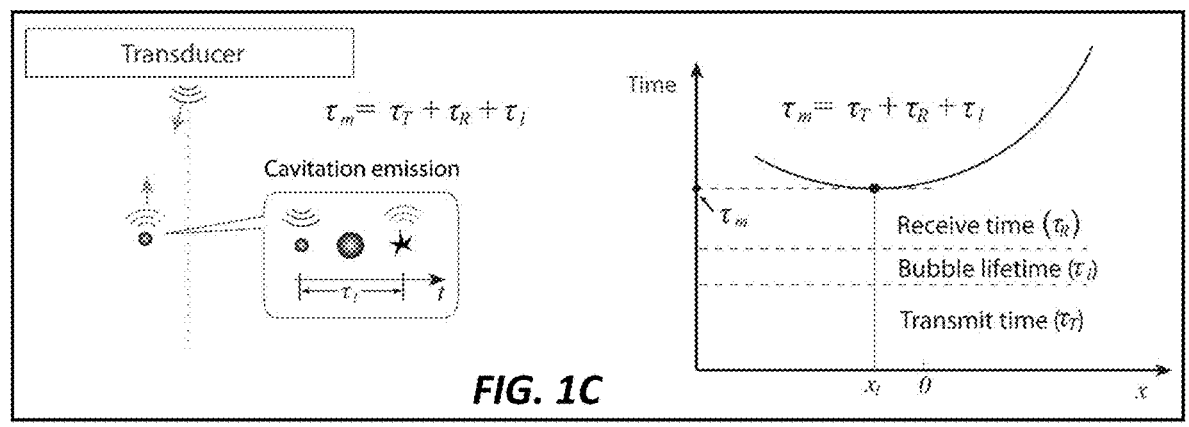

The "roundtrip transit time" of acoustic emissions from microbubbles is unknown because the microbubbles exhibit uncertainty in the time in which it may collapse in response to a therapeutic ultrasound pulse. This unknown time-delay between the therapeutic transmit event and the receive event is known as the bubble lifetime ($\tau_l$). Thus, the total roundtrip transit time between the transmitted therapy pulse and the received cavitation event is given by $\tau_m=\tau_{RX}+\tau_{TX}+\tau_l$, as illustrated in FIG. 1C. To apply the previous method to the localization of cavitating microbubbles, the dependence of the previous method on transit time must be eliminated from the equation. In addition, the new method must account for cavitation events that occur at locations off the beam axis.

Figure 2A:
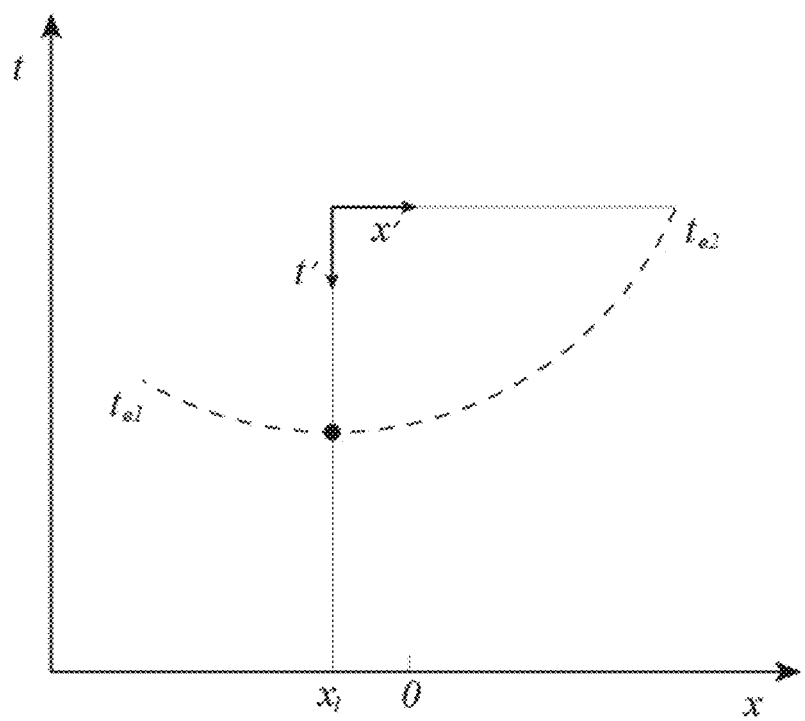
FIGS. 2A-2B show (2A) the arrival-time profile with respect to the new coordinate system (x', t'), given in terms of the time relative to the arrival time at the edge of the array furthest from the scatter ($t_{e2}$ in this example). The x coordinate is shifted to the x location of the leading edge of the profile. The center of the curvature in the new coordinate system indicates the location of the source ($z_t$). (2B) Relative arrival-time profile described using a transducer array. The arrival-time profile in the new coordinate system is described with the radius-of-curvature (R) of the arrival-time profile and the distance ($ct_1$) between the center of the curvature and x' for t'=0, expressed as R/c-$t_1$, according to the current invention.
Figure 2B:
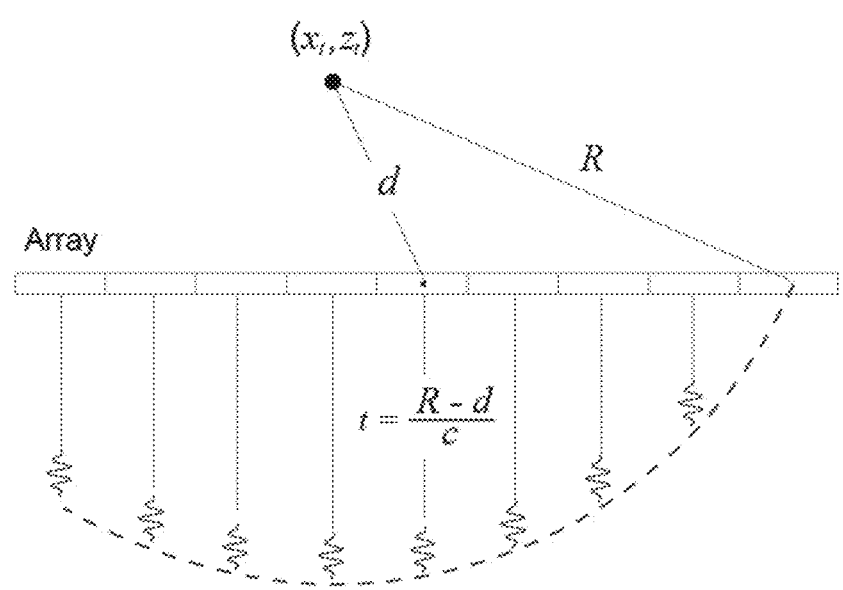

According to the current invention, a modified parabolic fit based on the geometrical characteristics of a spherical wave emission from the acoustic source incident on the surface of a linear transducer array is utilized to eliminate the dependence on transmit and receive timing. The modified parabolic fit requires a coordinate transformation applied to the arrival-time profile, t(x), of a wave from an unknown source location and time:

$$x'=x-x_l, \text{ and } t'=t_{e,max}-t, \tag{4}$$

where $x_l$ is the lateral location of the minimum receive time of the acoustic emission at the transducer surface and $t_{e,max}=\max(t_{e1}, t_{e2})$; $t_{e1}$ and $t_{e2}$ are the receive-times at the edges of the transducer. As shown in FIGS. 2A-2B, the receive times in the new coordinate system indicate the time-advance relative to the receive times at the edge of the transducer, expressed as $t'=R/c-t_t$, where $t_1=\sqrt{x'^2+y_t^2+z_t^2}/c$ is the propagation time from the acoustic source to x', R is the radius-of-curvature of the spherical wavefront, $z_t$ is the axial location of the acoustic source, and c is the sound speed. The receive-time profile in the new coordinate system can then be described by $$t'(x') = \frac{R}{c} - \frac{\sqrt{x'^2+y_t^2+z_t^2}}{c}. \quad (5)$$

Rearranging equation (5) and taking the square, one obtains $$(ct'-R)^2 = x'^2 + y_t^2 + z_t^2. \quad (6)$$

Equation (6) is then rearranged to obtain the $2^{nd}$ order polynomial describing the transducer element location as a function of arrival time:

$$x'^2(t') = c^2 t'^2 - 2cRt' + (R^2 - y_t^2 z_t^2). \quad (7)$$

Equation (7) is of the form $x'^2(t') = p_1 t'^2 + p_2 t' + p_3$, where $p_1 = c^2$, $p_2 = -2cR$, and $p_3 = R^2 - y_t^2 - z_t^2. \quad (8)$ Given the receive-time profile, a second-order polynomial fit to $x'^2(t')$ in the least-squares sense can be used to estimate the parameters in Equation (8), which can then be used to compute the radius of curvature of the sphere, R. From the coefficients of the parabola, the radius of curvature, and the assumption that $y_t \ll z_t$, the source location can be solved by $$c = \sqrt{p_1} \quad (9)$$
$$R = -\frac{p_2}{2c},$$
$$x_t = x_l + \text{sign}(t_{e1} - t_{e2}) \cdot |(w/2) - \sqrt{p_3}|, \text{ and}$$
$$z_t = \sqrt{R^2 - p_3},$$

where w is the width of the transducer aperture.

While the previous method described above was proposed as an approach to estimate the average speed of sound between the transducer and scattering point, this new method of the current invention is to localize multiple cavitation sources, which may include multiple cavitation events occurring simultaneously at nearby locations. For example, an illustration of cavitation occurring at three different locations at three unknown times within the focus is shown in FIG. 3A. The received waveforms sampled by the transducer array over time is composed of multiple wave patterns corresponding to each cavitation event in FIG. 3B.

The previous method obtains the arrival-time profile from an acoustic emission or scatterer by cross correlation of the received waveform in the aperture domain. In the current invention, multiple arrival-time profiles are extracted using a time-gated window for each scatterer. As shown in FIG. 3C, the time-gate window is represented by dashed lines and is chosen to encompass each wave pattern. A time-gated window is formed by first selecting N samples from the first element signal, $S_1$. Here, the time-gated window starts at a depth of $r_n$ samples, where $r_n = (n-1)N$ and n is an integer. The windowed signal is then cross-correlated with an N-point window at the same depth from the second element signal, $S_2$, as a function of axial sample lag l, where $l = -N, \ldots, +N$, using $$R(m=1, r_n, l) = \frac{\sum_{i=1}^{N} [S_1(r_n+i)] \cdot [S_2(r_n+i+l)]}{\sqrt{\sum_{j=1}^{N} [S_1(r_n+j)]^2 \cdot \sum_{k=1}^{N} [S_2(r_n+k+l)]^2}}, \quad (10)$$

The time-delay estimate between the elements is determined from the location of the maximum of $R_{1,2}$:

$l_{max} = \text{argmax}_{l \in L} R(m=1, r_n, l) = \Delta_{m=1,n}$ where L is the search region (from $-N$ to $+N$) and $\Delta_{m,n}$ is the time-delay estimate between m and (m+1) at a depth, $r_n$. For the time-delay estimate between $S_2$ and $S_3$, the time-gated windows for $S_2$ and $S_3$ are shifted by $\Delta_{m=1,n}$ corresponding to the previous time-delay estimate in addition to $r_n$ samples, i.e., $r_n + \Delta_{m=1,n}$. For further elements (m>3), the additional time-delay shift should be accumulated $(r_n + \Sigma_{k=1}^{m-1} \Delta_{k,n})$, to allow the time-gated window to be centered on the wavefront of interest, as shown in FIG. 3C. Using the accumulated time-delay shift, the cross correlation of an arbitrary pair of channel signals is determined by $$R(m, r_n, l) = \frac{\sum_{i=0}^{N-1} [S_m(r_n+\overline{\Delta}_{m,n}+i)] \cdot [S_{m+1}(r_n+\overline{\Delta}_{m,n}+i+l)]}{\sqrt{\sum_{j=0}^{N-1} [S_m(r_n+\overline{\Delta}_{m,n}+j)]^2 \cdot \sum_{k=0}^{N-1} [S_{m+1}(r_n+\overline{\Delta}_{m,n}+k+l)]^2}}, \quad (11)$$

where m is the channel number (m=1, ..., M) and $\overline{\Delta}_{m,n}$ is the accumulated time-delay ($\overline{\Delta}_{m,n} = \Sigma_{k=1}^{m-1} \Delta_{k,n}$ with $\overline{\Delta}_{1,n} = 0$ for m=1).

The accumulated time-delay, $\overline{\Delta}_{m,n}$, represents the arrival time relative to the reference element (m=1). The arrival-time profile for the cavitation signal is obtained by adding the accumulated time-delay to $r_n = (n-1)N$ samples; time zero is set immediately after the insonation pulse transmits. The arrival-time profile is represented by $$t_n = (r_n + \overline{\Delta}_{m,n})/F_s = [(n-1)N + \overline{\Delta}_{m,n}]/F_s, \quad (12)$$

where $F_s$ is the sampling frequency. The obtained arrival-time profiles in Equation (12) are then applied to the modified parabolic fit described previously to identify the location of the cavitation source.

To calculate cavitation magnitude at each cavitation source, the time-gated cavitation signals from the corresponding cavitation source are summed across the channels and then integrated in the time domain. The cavitation magnitude is expressed by $$I_n = \int_{(r_n+\overline{\Delta}_{m,n})/F_s}^{(r_n+N+\overline{\Delta}_{m,n})/F_s} \left| \sum_{m=1}^{M} d_m \cdot S_m(t) \right|^2 dt, \quad (13)$$
$$= \sum_{k=1}^{N} \left| \sum_{m=1}^{M} d_m \cdot S_m(r_n+k+\overline{\Delta}_{m,n}) \right|^2,$$

where $d_m$ is the distance from the scatter to $m^{th}$ element, M is the total number of transducer elements, N is the number of the samples, and the channel signals have been time-delayed according to the delays $\Delta_{m,n}$.

Turning now to the validation of the modified parabola fit, aperture domain signals from a grid of point scatterers were simulated with Field II; point scatteres were separated axially by 2 mm from 30 to 50 mm depth and laterally by 4 mm from −12 to 12 mm and each was simulated individually to avoid interaction of the pulse with the other scatterers. A 128-element transducer with a center frequency of 7.825 MHz was simulated having excitation pulses having 2 periods of a 7.825 MHz sinusoid with a Hanning weighting, and an impulse response having a two-cycle Hanning-weighted pulse (for both the transmit and receive apertures). Transmit focusing was applied directly at the location of each point scatterer, but no receive focusing was applied). In this case, the point scatterers mimic conventional scatterers from pulse-echo ultrasound. To mimick inertial cavitation sources (i.e. broadband acoustic emission source, which occurs when bubbles collapse a few microseconds after insonification), arrival times over the entire aperture were given a delay of 3 μs to simulate the bubble lifetime.

For source localization, three methods were compared: the previous method (where the estimated arrival times were subtracted by half the minimum arrival time, $\tau_m/2$); the previous method with an x-coordinate transformation (i.e. the x origin was shifted to the x location of the leading edge of the wavefront, as is described by the x-transform in Equation 4); and the cavitation source localization (CSL) method of the current invention the using modified parabola fit.

The first two methods are based on the estimated receive time. The estimation errors for the two types of the acoustic sources (point scatterers and cavitation sources) were calculated as the difference between the estimated receive time and the actual receive time $(z_t/c)$, i.e., $\tau_m/2-z_t/c$.

Experiments were performed in a tissue-mimicking vessel phantom containing a 2-mm diameter tube filled with a $3.5 \times 10^8$ MBs/ml concentration of microbubbles (BR38, Bracco Research, Geneva, Switzerland). Destruction pulses were applied with a P4-1 transducer (ATL) 1.8 MHz and passive cavitation signals were obtained from the individual elements of an L11-4 linear array transducer (ATL), 7.8 MHz, as illustrated in FIG. 4A. Both transducers were connected to a single Verasonics Vantage 256 research ultrasound system for synchronized control. This platform allows for electronic steering of the therapy focus and imaging with both B-mode and passive cavitation maps. B-mode images before and after bubble destruction are shown in FIG. 4B. The dashed ellipses in FIG. 4B indicate the focal spots of the therapy transducer (beamwidths: lateral: 1.5 mm, axial: 15 mm, and depth: 9 mm), each spaced laterally by 1.2 mm. Pressure amplitudes are applied in the range of 1-6 MPa.

Cavitation signals, induced by the low-frequency transducer emitting 5 cycle therapy pulses at a pulse repetition rate of 10 Hz, were passively detected by the high-frequency transducer with a sampling frequency of 31.2 MHz. Therapy pulses were electronically steered and applied to the prescribed 6 treatment spots; each spot received 40 therapy pulses for a combined total of 240 pulses over the 6 spots. The synchronized dual-probe system allows passive signal recording immediately after the therapy pulses were transmitted. The recorded signals were transferred to Matlab (MathWorks, Natick, Mass.) for offline processing.

In one aspect of the invention, a computing unit can include a field programmable gate array, a graphic processing unit, a computer, or an integrated circuit, which are optional platforms to do the computations.

The received element signals were upsampled by a factor of 8 before computing the arrival-time profiles of the received signals. Arrival-time profiles were selectively extracted for passive cavitation mapping based on fit quality. Arrival-time profiles with poor fit quality due to noise were excluded. The goodness of the parabola fit was determined with the r-square value and the root-mean-square error (rmse) of $x^2$ with respect to a parabola function, which has a unit of $mm^2$. Arrival-time profiles with r-square >0.9 and rmse <15 $mm^2$ were included in the cavitation mapping. Additionally, the radius-of-curvature (R; a unit of mm) of arrival-time profiles can be chosen for a specific range of interest of expected cavitation signals. In this example, a range of 30<R<80 was utilized because therapeutic ultrasound was applied to a region of −15<x<−5 mm and 35<z<50 mm (corresponding to 40<R<60 mm).

Figure 5:
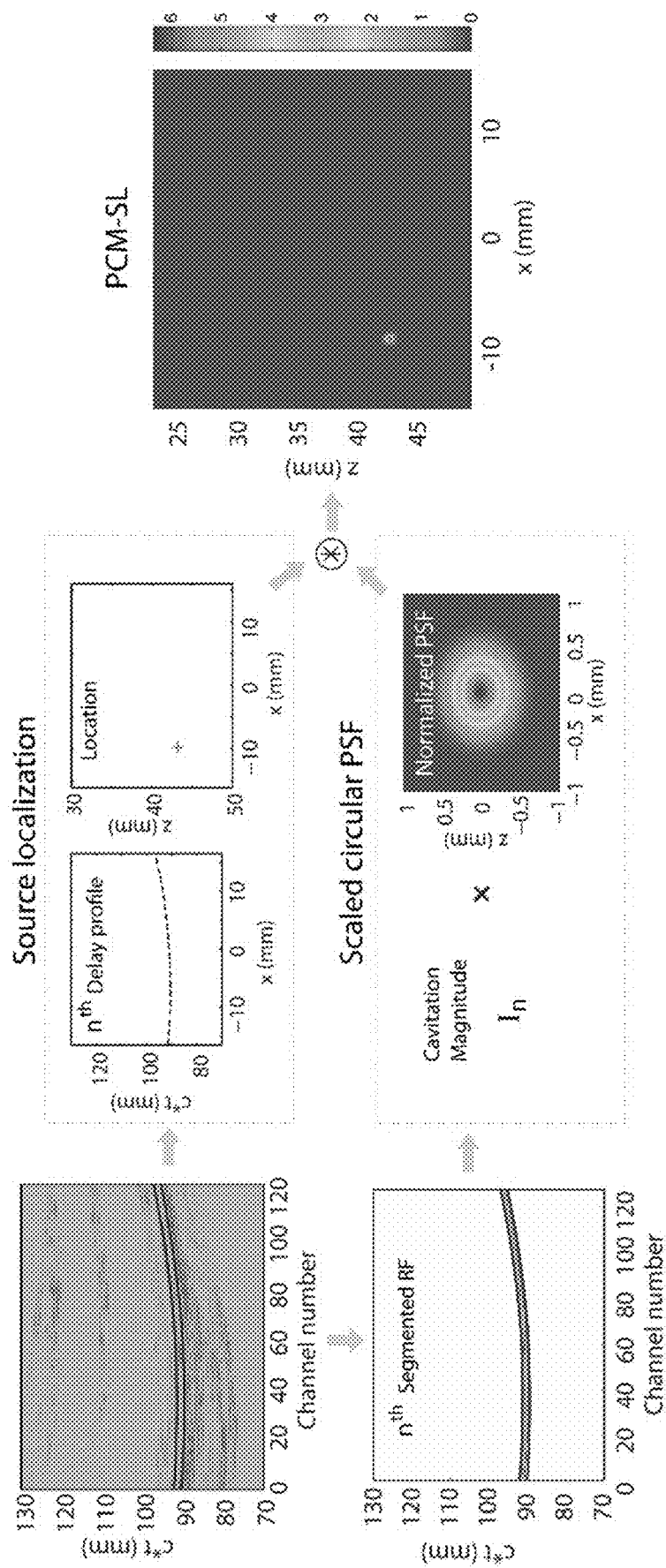
FIG. 5 shows a schematic diagram of passive cavitation mapping based on source localization (PCM-SL). The raw channel data shows $n^{th}$ time-window gated cavitation signals corresponding to a cavitation source. First, the arrival-time profile of the time-window gated signals is used for source localization. Then, the segmented cavitation signal is used for determining cavitation magnitude of the cavitation source ($I_n$). For cavitation mapping the point sources without area, we assume a circular point spread function (PSF) for the sources. The circular PSF with its peak amplitude scaled to the cavitation magnitude is convolved with the estimated source location, resulting in passive cavitation mapping, according to the current invention.

The process of cavitation mapping according to the current invention is illustrated in FIG. 5. The cavitation source location and magnitude were determined from the coefficients of the modified parabola fit. To construct a cavitation map showing both the cavitation source location and its magnitude, each cavitation event is given a finite area, which is assumed to be a circular range of uncertainty with the probability of cavitation exponentially decaying in a radial direction from 1 to 0 (described by a Gaussian function). The cavitation map is produced by convolving the source locations with the circular uncertainty range with a radius of 0.6 mm (full width at half maximum) and its peak amplitude scaled to the cavitation magnitude. The radius of 0.6 mm is arbitrarily chosen not to make too sparse while ensuring high mapping resolution. The radius corresponds to 3λ (λ=c/f, where f is the center frequency of the high-frequency transducer).

To study the effect of bubble-bubble interactions on PCM, aperture domain signals were simulated for multiple scatterers closely packed within a few wavelengths (using Field II). Here, the bubble-bubble interaction refers to interference of cavitation emission from closely-spaced bubbles rather than actual bubble-bubble hydrodynamics change. 11 scatterers were simulated with uniform lateral spacing of 0.05 mm (within a total lateral width of 0.5 mm from x=−0.25 to 0.25 mm) placed at a depth of z=30 mm. The scatterers are placed within the lateral beamwidth of the focused ultrasound. For both cases, the transmit pulse was focused at x=0, z=30 mm.

PCM based on time exposure acoustics (PCM-TEA) and PCM based on CSL (PCM-CSL) were performed using the simulated aperture domain signals.

Bubble lifetime is useful information that can be obtained from the CSL approach. Because the low-frequency transducer is synchronized with the high-frequency transducer, the minimum transit time $(\tau_m)$ is the sum of the transmit time $(\tau_{TX})$, bubble lifetime $(\tau_l)$, and receive time $(\tau_{RX})$, as illustrated in FIG. 1C. Once the cavitation location is identified, both the transmit and receive times can be evaluated and allow the bubble lifetime to be computed. The bubble lifetime $(\tau_l)$ can be estimated as $$\tau_l = \tau_m - (\tau_{RX} + \tau_{TX}), \quad (14)$$

where $(\tau_{RX}+\tau_{TX})$ is determined using the source location $(x_t, z_t)$, which is equivalent to the minimum transit time of waves from non-cavitation echo sources. The bubble lifetime $(\tau_l)$ should have a non-negative value and can be used as a criterion to exclude cavitation sources with non-physical bubble lifetimes, such as those due to overestimated z location or overestimated value of ($\tau_{RX}+\tau_{TX}$).

Turning now to the results for the cavitation source localization simulation, where FIG. 6 shows source localization using three different methods: the previous method described above, the previous method with the x-coordinate transformation from Equation (4), and the method of the current invent that includes the modified parabola fit. The estimated source locations (open circles) are plotted against the actual locations (solid stars). For the typical pulse-echo scatterers, the modified parabola fitting shows accurate localization of the pulse-echo acoustic sources (FIG. 6C), while the previous method results in poor localization (FIG. 6A), especially when the sources are located off-axis and closer to the transducer. Source localization by the previous method can be improved by applying the x-coordinate transformation (FIG. 6B).

For the cavitation-mimicking scatterers (FIG. 6D and FIG. 6E), the localization errors with the previous method become worse due to the delay from the bubble lifetime. The modified parabola fitting approach of the current invention demonstrates excellent localization of the cavitation sources (FIG. 6F).

Figure 7A:
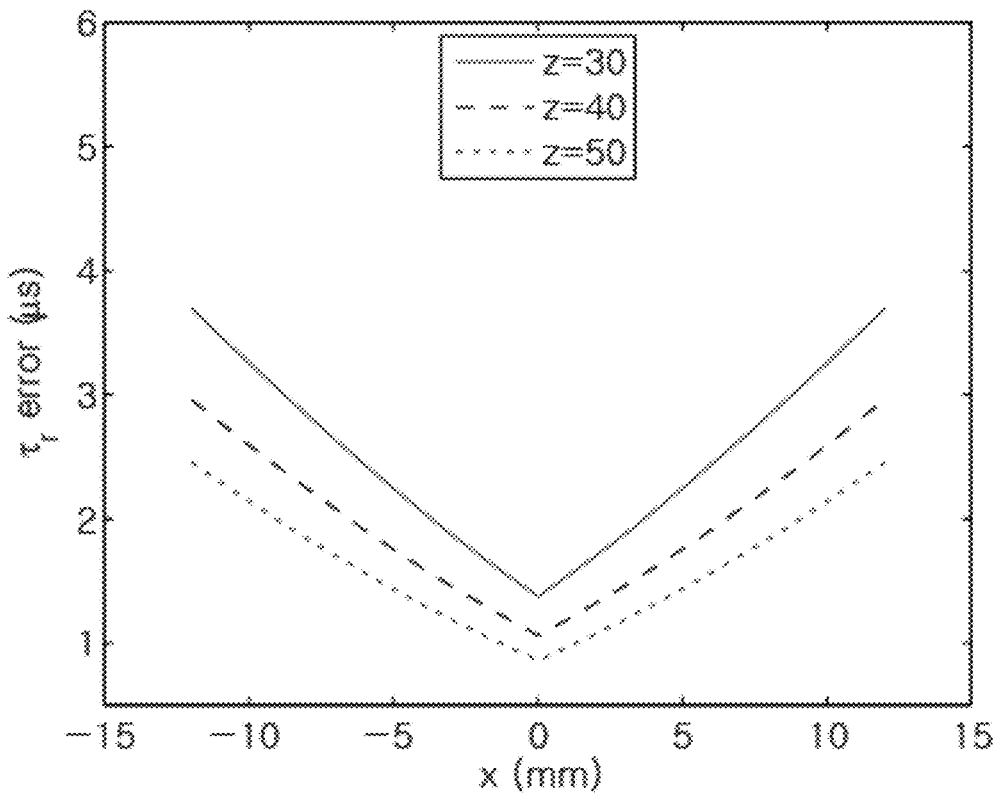
FIGS. 7A-7B show (7A) errors (ε) in the estimated receive times with respect to the actual receive time. The receive times are estimated as half the minimum transit time ($\tau_m/2$), while the actual receive time is determined with known axial location ($z_t/c$), i.e., $\varepsilon=\tau_m/2-z_t/c$. (a) Errors for pulse-echo scatterers. (7B) Errors for cavitation-mimicking sources with a lifetime of $\tau_l=3$ μs. The receive time errors increase for scatterers/emissions close to the transducer. For the cavitation-mimicking sources, the receive time errors increase by $\tau_l/2$, according to the current invention.
Figure 7B:
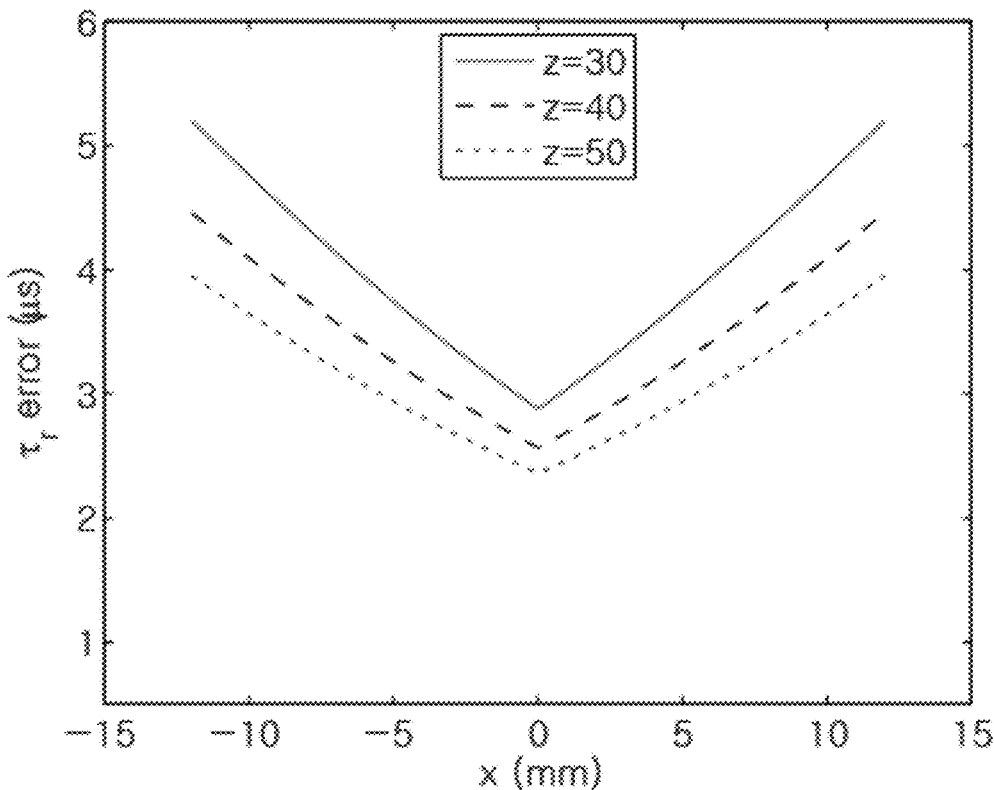

Poor estimation in the previous method is due to errors associated with isolation of the transmit event from the arrival-time profiles. The previous method is only accurate when a scatter is located on the center line and thus the transmit time is equal to the receive time, as illustrated in FIG. 1A. FIG. 7 shows estimation errors ($\tau_m/2 - z_t/c$) for the previous method. The receive time errors increase with scatters moving away from the axis and close to the transducer. For cavitation-mimicking scatters, the errors become worse due to the unknown bubble lifetime.

FIG. 8A shows an example of the raw RF channel data used in the proposed passive cavitation mapping method. The channel domain signals, produced by a therapy pulse, exhibit the signature of multiple wavefronts emitted from bubbles within the focal volume in a flow channel. FIGS. 8A and 8C show all of the time-window gates and their corresponding arrival-time profiles, respectively. The extracted arrival-time profiles consist of some profiles with smooth parabola curves and others with noisy curves. The noisy arrival-time profiles were filtered based on their goodness of fit (r-squared value >0.9), as shown in FIG. 8D. While this filter excluded most noisy profiles, additional filtering was applied to profiles having an rmse >15 mm² (e.g. the labelled profiles in FIG. 8D). The results of this secondary filtering are plotted in FIG. 8E. Lastly, a third filter was applied to eliminate profiles with a radius of curvature, R (Eq. 7), outside the range 30<R<80 mm for source localization, as shown in FIG. 8F, because these signals appear outside the displayed area of the image.

Figure 9A:
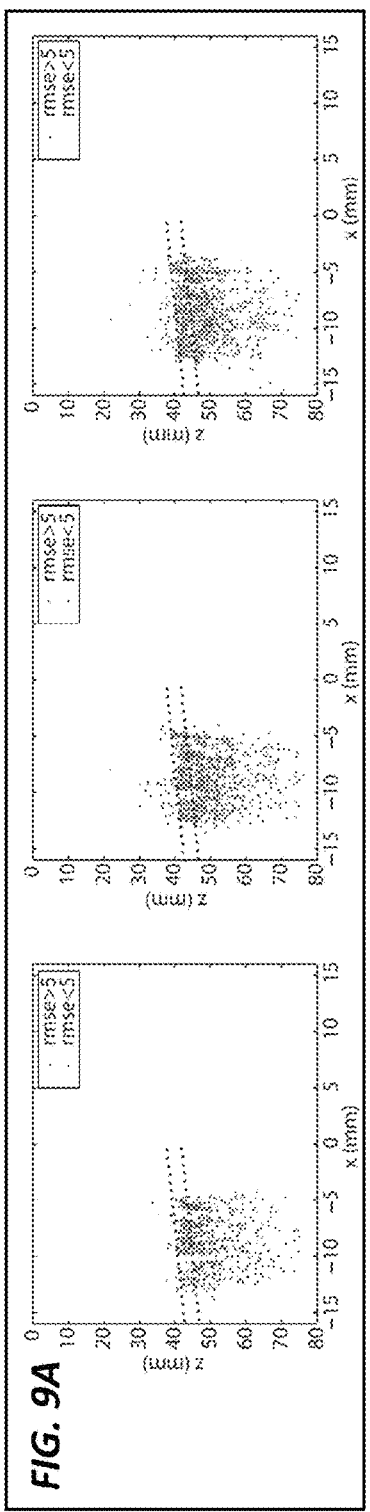
FIG. 9A-9C show (9A) Source localization for increasing transmit voltage (from left to right: 30, 50, and 70 V). (9B) Corresponding cavitation magnitude at each cavitation source and (9C) cavitation intensity and mapping. The dashed line indicates the flow channel of 2 mm in diameter. The passive cavitation maps are obtained with convolution of the cavitation magnitude at its source point with an assumed circular point spread function (PSF) with a radius of 0.6 mm (full width at half maximum, FWHM), corresponding to 3λ (λ=c/f, where f is the center frequency of the transducer). The grid spacing of the image is 0.1 mm.

Turning now to the passive cavitation mapping, the selected arrival-time profiles based on fit quality and radius of curvature are used to find individual source locations. FIG. 9A shows estimated sources with higher fit qualities (0<rmse<5 mm²; red dot) are mostly located within the 2-mm diameter tube, while sources with lower fit qualities (5<rmse<15 mm²) are located outside the tube, preferentially below the tube. As cavitation bubbles are present only within the tube, the location of the sources from lower quality parabolic fits are inaccurate.

Figure 9B:
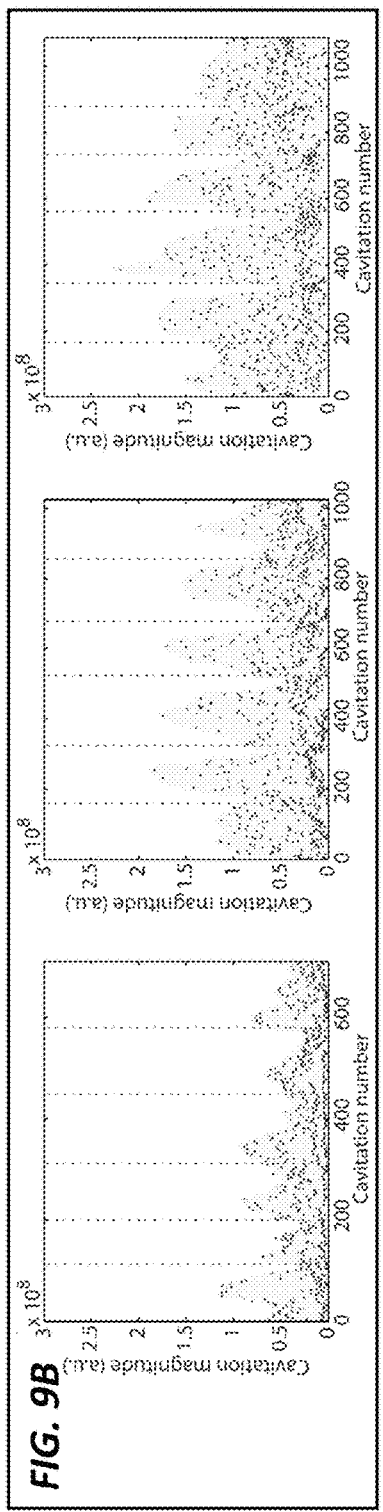

The cavitation magnitude of each source is calculated using the time-window gate corresponding to the source and plotted FIG. 9B. The cavitation numbers were divided into six divisions corresponding to the six therapy focal spots. The cavitation magnitudes increase with pressure amplitude. The cavitation magnitudes were lower because most of the bubbles were destroyed by the end of each treatment.

Figure 9C:
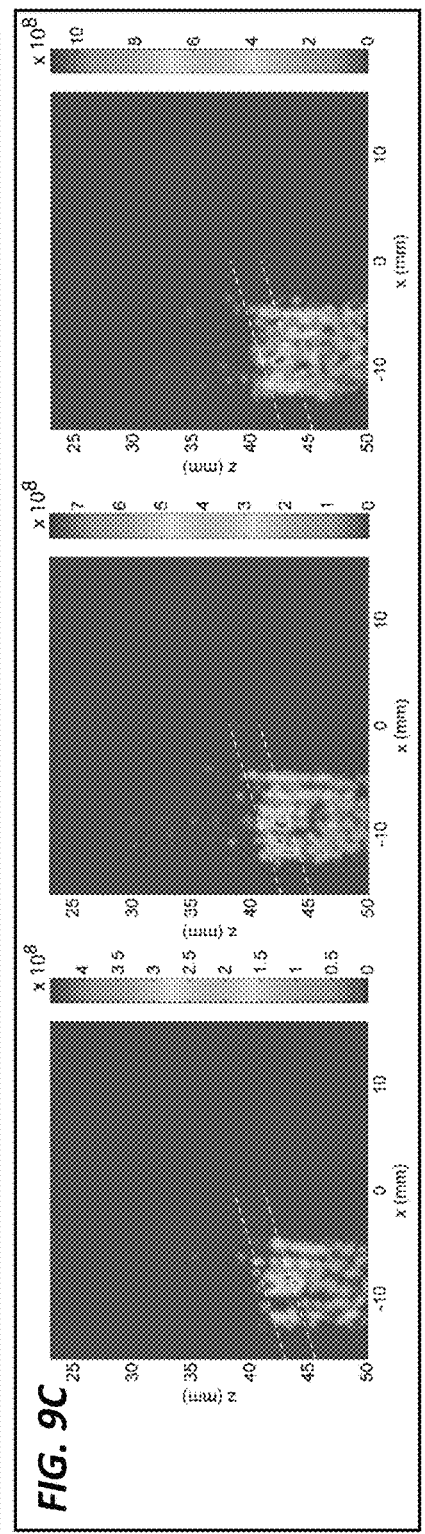

By using the estimated source locations (FIG. 9A) and the calculated cavitation magnitudes (FIG. 9B), passive cavitation maps were constructed, as shown in FIG. 9C. The cavitation maps show high cavitation magnitudes within the tube, but still exhibit some tail artifacts beyond the tube, which are created by the sources with higher rmse, as seen in FIG. 9A.

A simulated cavitation map using time exposure acoustics (TEA) is shown in FIG. 10A for a single acoustic source. The axial length is calculated to be approximately 9λ (FWHM). In FIG. 10B, the simulated PCM-TEA for the closely-spaced scatters exhibits an axial length of 24.5λ. In the PCM-CSL approach, the multiple sources appear as a single source, because they produce only a single arrival-time profile due to the interference of the source signals, much like that for diffuse scatterers in pulse-echo imaging. Unlike the single point source case (FIG. 10B), the closely-packed sources lead to overestimation of their locations through the CSL approach, which is the same as the peak shift (Δz=0.65 mm) in the PCM-TEA. Instead of underestimation, such overestimation is the most likely because overlapped wavefronts cause larger radius-of-curvature than that of each individual wavefront (Eq. 9, $z_t \sim R$). Thus, these bubble-bubble interactions, or more precisely described as the superposition of waves emitted from closely-located bubbles, can explain the tail artifacts observed in both PCM-TEA and PCM-CSL techniques.

The overestimated z location due to the bubble-bubble interaction results in increased rmse of 25 mm² (3 for a single scatterer) and negative bubble lifetime. The bubble lifetime and rmse can be used to exclude cavitation signals arising from the bubble-bubble interaction.

Figure 11A:
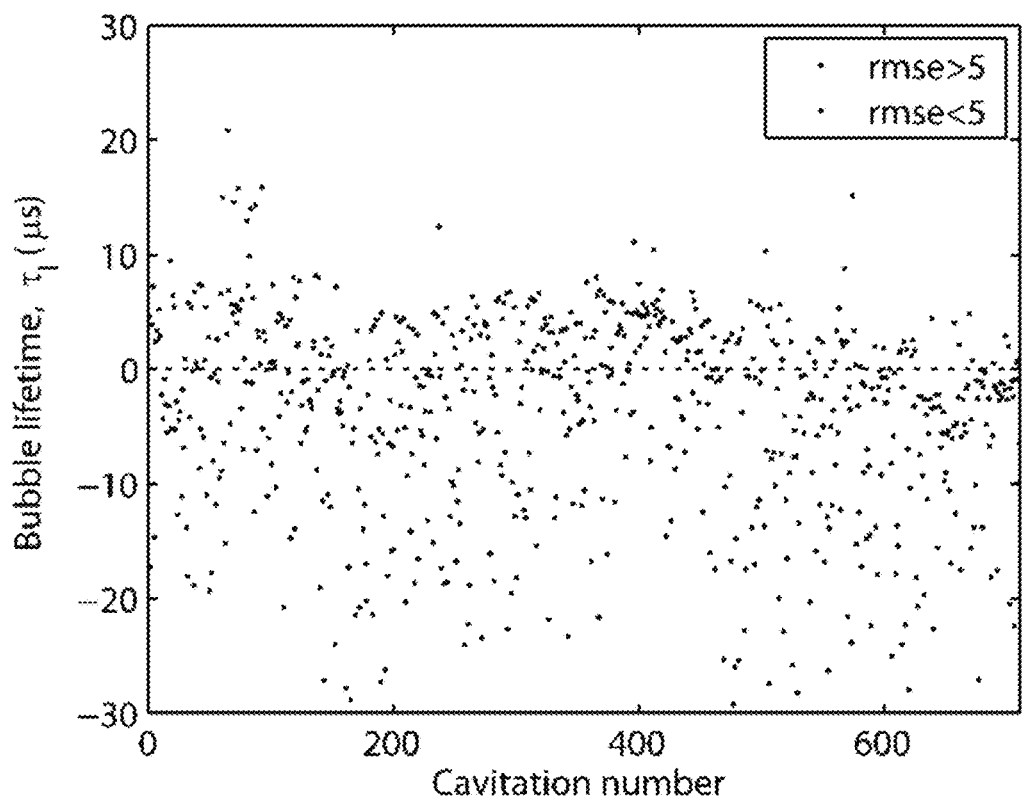
FIGS. 11A-11B show estimated bubble lifetimes for different pressure amplitudes for 30, 50 V (11A) and (11B). The dots below the zero line generally indicate low fit qualities (rmse >5), while the dots above the zero line generally high fit qualities (rmse <5). The bubble lifetimes for low fit qualities tend to have negative bubble lifetime, which is physically unrealistic and is believed due to bubble-bubble interactions. The average positive bubble lifetime for 30 V is 6.26±4.6 µs, while for 50 V it is slightly increased to 7.69±6.1 µs, according to the current invention.
Figure 11B:
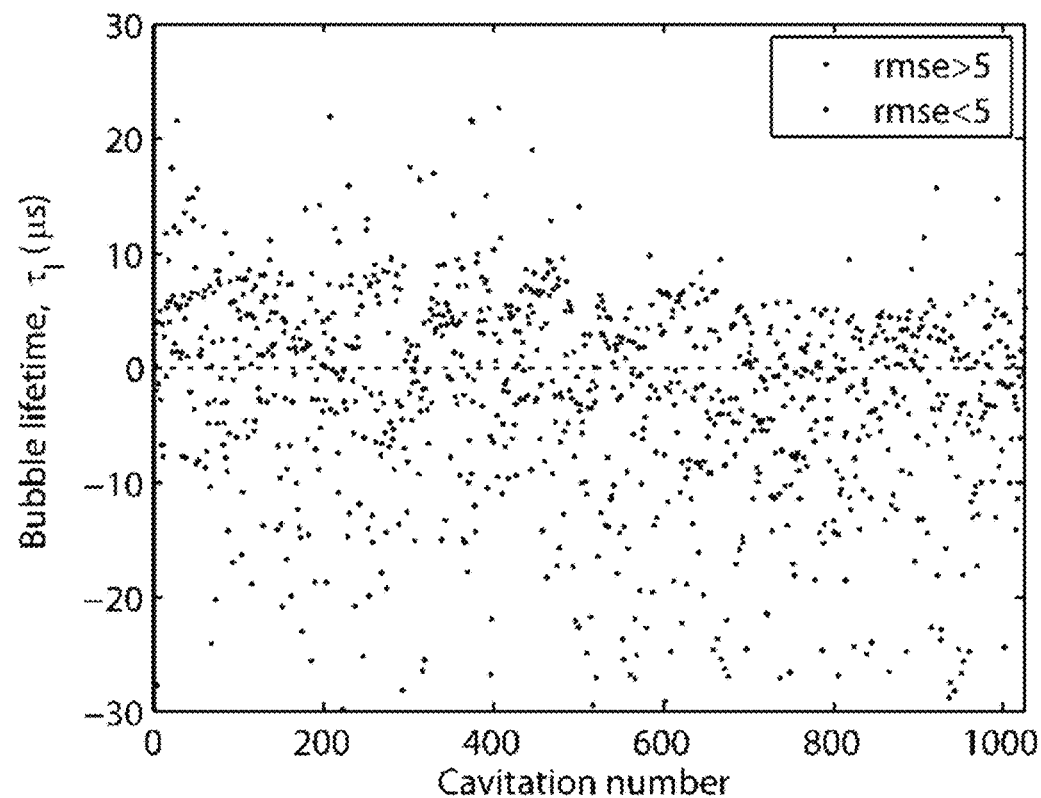

Regarding bubble lifetime analysis, as a negative bubble lifetime can arise from the bubble-bubble interaction, the calculated bubble lifetime can be used as a criterion to eliminate the tail artifact by the bubble-bubble interaction. FIGS. 11A-11B show the estimated bubble lifetime for two different therapy voltages (30, 50 V). For both voltages, there exists several cavitating bubbles having negative bubble lifetimes, which is physically unrealistic. Note that most cavitating bubbles with a low quality fit (rmse >5 mm²) have negative bubble lifetimes, with only a few cavitating bubbles with a high quality fit (rmse <5 mm²) having a negative bubble lifetime. Increasing the voltage increased the average value of the positive bubble lifetimes from 6.26±4.6 µs to 7.69±6.1 µs.

Figures 12A, 12B, 12C:
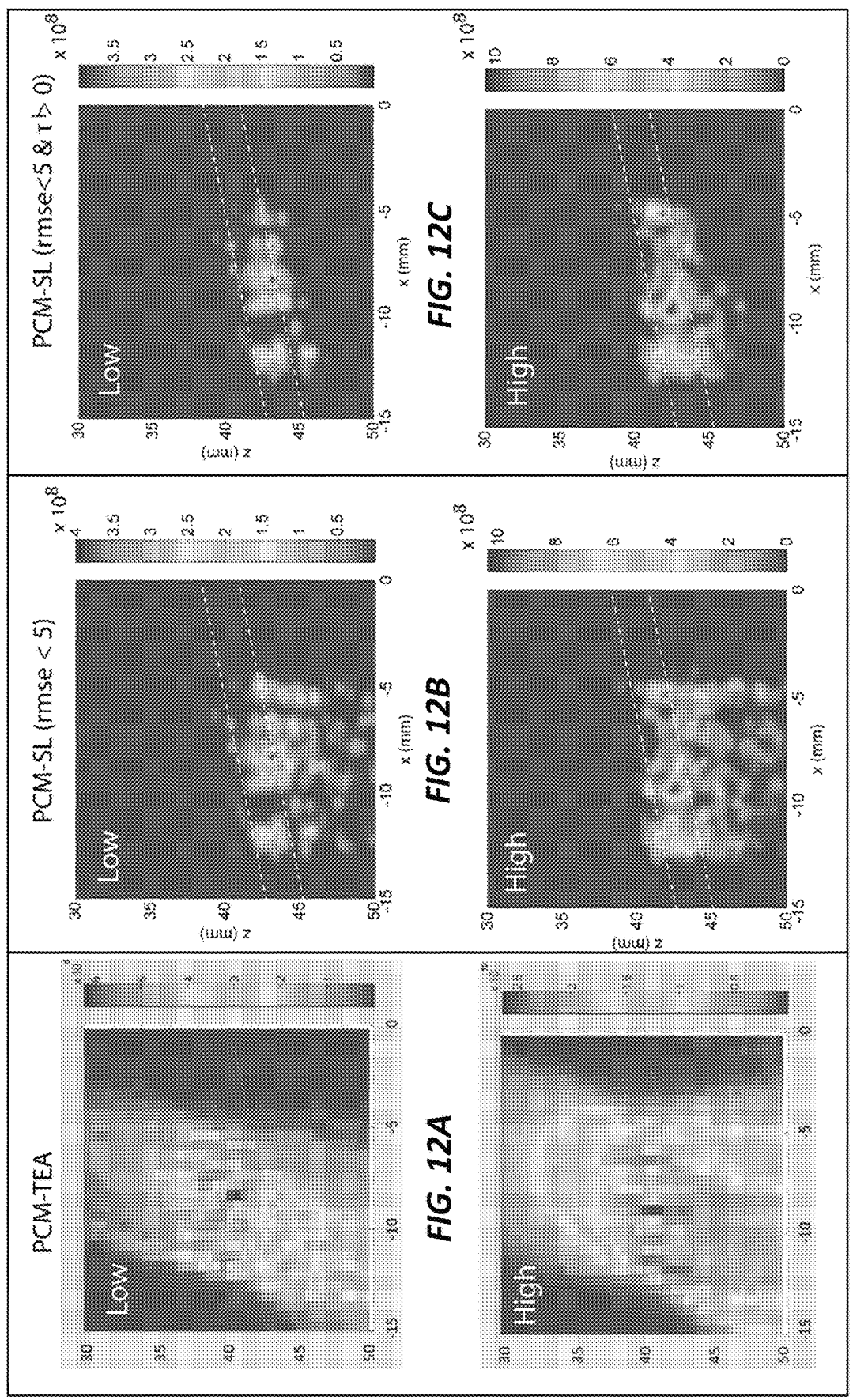
FIGS. 12A-12C show (12A) passive cavitation mapping using time exposure acoustics (PCM-TEA) for low (top) and high-pressure amplitudes (bottom). (12B) Passive cavitation mapping using source localization (PCM-SL) for rmse <5. (12C) PCM-SL for rmse <5 and $\tau_l>0$, according to the current invention.

PCM-CSL shows improved axial resolution by addressing the issue associated with the finite point spread function, but there still remains some tail artifact. FIG. 12A shows PCM-TEA and the PCM-CSL method of the current invention were compared for two pressure amplitudes. In FIG. 12B, the low quality fits (rmse >5 mm²) are removed and PCM-CSL shows reduced tail artifacts compared to PCM-TEA. In FIG. 12C, sources with a negative bubble lifetime have also been eliminated from the PCM-CSL image (i.e. rmse <5 mm² and $\tau_t$>0) and shows further reduction in tail artifact as the cavitation signals are mostly confined to within the channel. At high pressure amplitudes, PCM-TEA resulted in more distinct tail artifacts due to stronger bubble-bubble interactions, whereas PCM-CSL still provides acceptable spatially-confined cavitation mapping.

For a general discussion, this technique uses a modified parabolic fit to the squared arrival times to localize the cavitation source in the x-z plane, assuming a constant speed of sound. The source signal can then be placed into a passive cavitation image, where the magnitude can be included. Because the cavitation signals from multiple time-gated windows are utilized, the cavitation signals occurring at the same location can be accumulated in the passive cavitation image for quantification of a cavitation dose.

The long tail artifacts in the point spread function of the conventional PCM-TEA approach arises from the imperfect spatial filtering of cavitation signals due to the fixed-focusing of the receive-beamforming process. A consequence of this artifact is that the total cavitation dose is overestimated from all other locations because of spreading of the system response (FIGS. 10A-10B and FIG. 12A). In the proposed PCM-CSL approach, the cavitation signals are isolated in the receive channel data and are not subjected to the spatial filtering in the fixed-focus receive-beamforming process, thereby confining the estimated cavitation dose to the uncertainty region. In addition, because the source localization technique does not require receive beamforming, the system can adapt to the position of the source signal. For the simulated ideal conditions in FIG. 6, the method was shown to accurately localize cavitation signals regardless of their position. Therefore, this approach is well suited to all types of passive cavitation mapping systems and is not limited by transducer configuration (e.g. co-aligned axis) or transducer type (e.g. linear, curvilinear, or phased array). In PCM-TEA methods that rely on receive beamforming, sources located off the beam axis (such as cavitation from sidelobes) are only well detected if the beams are steered in a direction orthogonal to the source wavefront. Thus, receive-beamforming PCM-TEA-based approaches require phased arrays to effectively detect off-axis cavitation signals because of the limited angular steering of linear and curvilinear arrays.

The time-gating approach to extraction of multiple arrival-time profiles works well for wavefronts that do not overlap with one another, but may have some difficulties in extracting wavefronts that interfere with each other. To minimize wavefront interference, principle component analysis could be utilized prior to wavefront gating and arrival-time estimation in order to isolate individual bubble signals or groups of bubble signals with similar arrival-time characteristics.

In addition, the approach may benefit from smoothing the arrival-time profiles before performing the coordinate transformation.

Alternatively, without the coordinate transformation, the previous method can be used by incorporating iterative approaches where unknown times, such as transmit time and bubble lifetime, are assumed and adjusted until the rmse is minimized.

The bubble lifetime analysis can effectively remove the tail artifact produced by the bubble-bubble interaction. Although this approach improves the "visual localization" of the cavitation events to within the boundaries where cavitation should be expected (e.g. within the channel region), it may eliminate valid cavitation data that have poor localization estimates. For example, a bubble cloud may have a negative bubble lifetime due to the uncertainty in its localization. This issue could be critical for high bubble concentrations in phantoms. However, for moderate-to-low bubble concentrations often observed in vivo, the bubble-bubble interaction effect would be minimized, as in the case of drug delivery to tumors where the concentration of bubbles at the target site may be low.

PCM-TEA cannot discern the bubble-bubble interaction effect. However, the PCM-SL approach could be utilized to include or exclude the contribution of the bubble-bubble interaction to PCM, or further modified to better differentiate cavitation signals resulting from bubble-bubble interaction. For example, the bubble lifetime analysis can be used to iteratively correct overestimated z locations resulting from the bubble-bubble interaction. The bubble lifetime analysis could also provide other useful information such as bubble dynamics. For example, negative bubble lifetime could be used to indicate bubble-bubble interaction and positive bubble lifetimes of individual bubbles could be used to describe bubble dynamics and estimate maximum bubble radius, because bubble lifetime increases linearly with the maximum bubble radius. For large bubble lifetimes, and thereby large maximum bubble radii, cavitation-induced mechanical effects (or sonoporation) are maximized. In this sense, bubble lifetime can be used as a measure of cavitation dose, which is similar to inertial cavitation dose based on cavitation-induced acoustic emission.

In conclusion, the invention provides a new passive cavitation mapping (PCM) algorithm based on source localization. This approach can realize high-resolution PCM and achieve improved localization of cavitation than conventional PCM-TEA techniques. In addition, described herein is a technique that can be utilized to provide information about bubble-bubble interactions and bubble dynamics.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example the arrival or receive-time profiles can be computed using quality metrics or techniques other than cross-correlation, such as phase-shift estimation, or sum absolute difference techniques. In addition, other forms of principle component analysis, such as those based on singular value decomposition, can be used to isolate cavitation signals instead of or in addition to time gating. Methods that update or improve the coefficients in the modified parabolic fit can also be used. For example, computing average or local speed of sound or eliminating phase aberrations to improve the source localization can be used.

All such variations are considered to be within the scope and spirit of the present invention as defined by the following claims and their legal equivalents.

What is claimed:
1. A passive cavitation mapping method, comprising:
a) capturing, using an ultrasound scanning device, channel signals from at least one ultrasound transducer in an array of ultrasound transducers;
b) isolating, using said ultrasound scanning device, cavitation signals in said channel signals, wherein said isolating comprises using a filtering method;
c) time-gating said channel signals about said cavitation signals;
d) computing time-delays between neighboring said cavitation signals in adjacent said channel signals, wherein said time-delays of said cavitation signals are accumulated to obtain arrival times of said cavitation signals;
e) computing a modified parabolic fit to the square of said arrival times, wherein said modified parabolic fit comprises a coordinate transformation using an x location of a leading edge of wavefronts of said cavitation signals and a maximum arrival time of said cavitation signals;
f) extracting a location of a cavitation signal source at a point (x, z) in said coordinate transformation;

g) computing a cavitation magnitude for each said cavitation signal source;
h) creating a passive cavitation map by convolving said cavitation magnitude and said location with an uncertainty function; and
i) using said passive cavitation map for therapeutic ultrasound applications.

2. The method of claim 1, wherein said uncertainty function comprises a circularly Gaussian function.

3. The method of claim 1 further comprising eliminating spurious cavitation signals, using said computer, based on a fit quality of said modified parabola, to produce non-eliminated cavitation signals.

4. The method of claim 3 further comprising calculating a bubble lifetime of each said non-eliminated cavitation signals, using said computer, and eliminating cavitation signals that have negative bubble lifetimes.

\* \* \* \* \*